(12) United States Patent
Du

(10) Patent No.: US 11,147,474 B2
(45) Date of Patent: Oct. 19, 2021

(54) LIVING BODY DETECTING METHOD AND APPARATUS, DEVICE AND COMPUTER STORAGE MEDIUM

(71) Applicant: BAIDU ONLINE NETWORK TECHNOLOGY (BEIJING) CO., LTD., Beijing (CN)

(72) Inventor: Yajie Du, Beijing (CN)

(73) Assignee: BAIDU ONLINE NETWORK TECHNOLOGY (BEIJING) CO., LTD., Beijing (CN)

(*) Notice: Subject to any disclaimer, the term of this patent is extended or adjusted under 35 U.S.C. 154(b) by 727 days.

(21) Appl. No.: 16/111,544

(22) Filed: Aug. 24, 2018

(65) Prior Publication Data

US 2019/0059786 A1 Feb. 28, 2019

(30) Foreign Application Priority Data

Aug. 25, 2017 (CN) .......................... 201710743630.1

(51) Int. Cl.
*A61B 5/097* (2006.01)
*A61B 5/1171* (2016.01)
*G06K 9/00* (2006.01)

(52) U.S. Cl.
CPC ............ *A61B 5/097* (2013.01); *A61B 5/1176* (2013.01); *G06K 9/00221* (2013.01); *G06K 9/00288* (2013.01); *G06K 9/00302* (2013.01); *A61B 2562/029* (2013.01); *A61B 2562/046* (2013.01);
(Continued)

(58) Field of Classification Search
CPC . A61B 5/097; A61B 5/1176; A61B 2562/162; A61B 2562/046; A61B 2562/029; A61B 5/00; A61B 5/082; A61B 5/1116; A61B 5/113; G06K 9/00221;
(Continued)

(56) References Cited

U.S. PATENT DOCUMENTS

| | | | |
|---|---|---|---|
| 9,288,840 B2* | 3/2016 | Park ...................... | G06F 3/011 |
| 9,595,143 B1 | 3/2017 | Ashenfelter et al. | |
| 9,734,316 B2* | 8/2017 | Singh ................... | A61B 5/0205 |

(Continued)

FOREIGN PATENT DOCUMENTS

| | | |
|---|---|---|
| CN | 1638695 A | 7/2005 |
| CN | 103100136 A | 5/2013 |

(Continued)

OTHER PUBLICATIONS

Search Report of Chinese Appln. No. 201710743630.1 dated Jun. 2, 2020, 2 pages.

(Continued)

*Primary Examiner* — Wesley J Tucker
(74) *Attorney, Agent, or Firm* — Brooks Kushman P.C.

(57) ABSTRACT

The present disclosure provides a living body detecting method and apparatus, and a computer device, wherein the method comprises: obtaining data of a user's same breathing act through a humidity sensor array and a camera respectively; determining the user's face posture according to data obtained by the humidity sensor array and data obtained by the camera respectively; comparing the determined face postures, and judging whether the user is a living body according to a comparison result. The technical solution of the present disclosure can implement living body detection for the user.

24 Claims, 5 Drawing Sheets

(52) U.S. Cl.
CPC .................. *A61B 2562/162* (2013.01); *G06K 2009/00328* (2013.01)

(58) Field of Classification Search
CPC ........... G06K 9/00302; G06K 9/00288; G06K 2009/00328
See application file for complete search history.

(56) References Cited

U.S. PATENT DOCUMENTS

| | | | |
|---|---|---|---|
| 2010/0227640 A1* | 9/2010 | Kim | H04M 19/04 455/550.1 |
| 2011/0004327 A1* | 1/2011 | Bonnat | G06F 3/0346 700/83 |
| 2014/0055346 A1* | 2/2014 | Boni | G06F 3/0485 345/156 |
| 2014/0276104 A1* | 9/2014 | Tao | A61B 5/1128 600/476 |
| 2016/0150981 A1* | 6/2016 | Baker | A61B 5/6819 600/479 |
| 2016/0277397 A1 | 9/2016 | Watababe | |
| 2017/0157435 A1* | 6/2017 | Choi | A41D 13/1107 |
| 2018/0101721 A1* | 4/2018 | Nienhouse | B60K 28/063 |
| 2019/0358473 A1* | 11/2019 | Szasz | G08B 21/182 |
| 2020/0177537 A1* | 6/2020 | Chang | H04L 51/26 |
| 2020/0342245 A1* | 10/2020 | Lubin | G06K 9/0061 |
| 2021/0117708 A1* | 4/2021 | Sandhan | G06K 9/00288 |

FOREIGN PATENT DOCUMENTS

| | | |
|---|---|---|
| CN | 103761465 A | 4/2014 |
| CN | 103841258 A | 6/2014 |
| CN | 104392204 A | 3/2015 |
| CN | 104463237 A | 3/2015 |
| CN | 105224924 A | 1/2016 |
| CN | 105718874 A | 6/2016 |
| CN | 105761080 A | 7/2016 |
| CN | 105787420 A | 7/2016 |
| CN | 105813562 A | 7/2016 |
| CN | 105816176 A | 8/2016 |
| CN | 106485232 A | 3/2017 |
| CN | 106725490 A | 5/2017 |
| CN | 106845345 A | 6/2017 |
| EP | 2677490 A4 | 11/2016 |

OTHER PUBLICATIONS

Chinese Office Action dated Dec. 17, 2019, for related Chinese Appln. No. 201710743630.1; 9 Pages.
Chinese Search Report dated Dec. 4, 2019 for related Chinese Appln. No. 201710743630.1; 4 Pages.

* cited by examiner

LIVING BODY DETECTING METHOD AND APPARATUS, DEVICE AND COMPUTER STORAGE MEDIUM

The present application claims the priority of Chinese Patent Application No. 201710743630.1, filed on Aug. 25, 2017, with the title of "Living body detecting method and apparatus, device and computer storage medium". The disclosure of the above applications is incorporated herein by reference in its entirety.

FIELD OF THE DISCLOSURE

The present disclosure relates to biological feature recognition technologies, and particularly to a living body detecting method and apparatus, a device and a computer storage medium.

BACKGROUND OF THE DISCLOSURE

In the prior art, upon scenarios such as airport security check and remotely-handled financial business, face recognition can only be used to recognize whether the user is the user himself, but cannot effectively verify whether the current user is a living body. Therefore, it is desirable to provide a method of performing living body detection.

SUMMARY OF THE DISCLOSURE

In view of the above, the present disclosure provides a living body detecting method and apparatus, a device and a computer storage medium, to implement living body detection for the user.

A technical solution employed by the present disclosure to solve technical problems is to provide a living body detecting method, the method comprising: obtaining data of a user's same breathing act through a humidity sensor array and a camera respectively; determining the user's face posture according to data obtained by the humidity sensor array and data obtained by the camera respectively; comparing the determined face postures, and judging whether the user is a living body according to a comparison result.

According to a preferred embodiment of the present disclosure, the humidity sensor array comprises a preset number of humidity sensors which are arranged in a specific shape.

According to a preferred embodiment of the present disclosure, the arrangement in a specific shape comprises: even arrangement along a spherical crown in a concentric circle form.

According to a preferred embodiment of the present disclosure, the obtaining data of the user's breathing act through the humidity sensor array comprises: obtaining humidity change distribution data of the humidity sensor array caused by the user's breathing act at a specific location.

According to a preferred embodiment of the present disclosure, the humidity sensor array comprises a preset number of humidity sensors which are arranged evenly along a spherical crown in a concentric circle form; the specific location is a location nearby a spherical center of the spherical crown.

According to a preferred embodiment of the present disclosure, the determining the user's face posture according to data obtained by the humidity sensor array comprises: determining location information of the humidity sensors in the humidity sensor array that humidity change values exceed a preset threshold; according to the specific location and locations of the determined humidity sensors, determining space vectors pointing from the specific location to the locations of the determined humidity sensors; determining the user's face posture according to the space vectors.

According to a preferred embodiment of the present disclosure, the determining the user's face posture according to data obtained by the humidity sensor array comprises: determining identification information of humidity sensors in the humidity sensor array that humidity change values exceed a preset threshold; determining the user's face posture according to a correspondence relationship between pre-configured identification information and the face posture.

According to a preferred embodiment of the present disclosure, the method further comprises: prompting the user to perform detection again if the humidity sensor array does not include humidity sensors that humidity change values exceed the present threshold.

According to a preferred embodiment of the present disclosure, if it is determined that there are a plurality of humidity sensors that the humidity change values exceed the preset threshold in the humidity sensor array, the method comprises: according to a preset rule, selecting one humidity sensor from the plurality of humidity sensors to determine the user's face posture; or using the plurality of humidity sensors to determine the user's face posture range.

According to a preferred embodiment of the present disclosure, the method further comprises: using the data obtained by the camera to perform face recognition to determine the user's identity.

According to a preferred embodiment of the present disclosure, the comparing the determined face postures and judging whether the user is a living body according to a comparison result comprises: judging whether the determined face postures are consistent, and determining that the user is a living body if the determined face postures are consistent.

A technical solution employed by the present disclosure to solve technical problems is to provide a living body detecting apparatus, the apparatus comprising: an obtaining unit configured to obtain data of a user's same breathing act through a humidity sensor array and a camera respectively; a determining unit configured to determine the user's face posture according to data obtained by the humidity sensor array and data obtained by the camera respectively; a judging unit configured to compare the determined face postures, and judge whether the user is a living body according to a comparison result.

According to a preferred embodiment of the present disclosure, the humidity sensor array comprises a preset number of humidity sensors which are arranged in a specific shape.

According to a preferred embodiment of the present disclosure, the arrangement in a specific shape comprises: even arrangement along a spherical crown in a concentric circle form.

According to a preferred embodiment of the present disclosure, upon obtaining data of the user's breathing act through the humidity sensor array, the obtaining unit specifically performs: obtaining humidity change distribution data of the humidity sensor array caused by the user's breathing act at a specific location.

According to a preferred embodiment of the present disclosure, the humidity sensor array comprises a preset number of humidity sensors which are arranged evenly along a spherical crown in a concentric circle form; the specific location is a location nearby a spherical center of the spherical crown.

According to a preferred embodiment of the present disclosure, upon determining the user's face posture according to data obtained by the humidity sensor array, the determining unit specifically performs: determine location information of the humidity sensors in the humidity sensor array that humidity change values exceed a preset threshold; according to the specific location and locations of the determined humidity sensors, determine space vectors pointing from the specific location to the locations of the determined humidity sensors; determine the user's face posture according to the space vectors.

According to a preferred embodiment of the present disclosure, upon determining the user's face posture according to data obtained by the humidity sensor array, the determining unit specifically performs: determine identification information of humidity sensors in the humidity sensor array that humidity change values exceed a preset threshold; determine the user's face posture according to a correspondence relationship between pre-configured identification information and the face posture.

According to a preferred embodiment of the present disclosure, the apparatus further comprises a re-detection unit configured to prompt the user to perform detection again if the humidity sensor array does not include humidity sensors that humidity change values exceed the present threshold.

According to a preferred embodiment of the present disclosure, if it is determined that there are a plurality of humidity sensors that the humidity change values exceed the preset threshold in the humidity sensor array, the determining unit specifically performs: according to a preset rule, select one humidity sensor from the plurality of humidity sensors to determine the user's face posture; or use the plurality of humidity sensors to determine the user's face posture range.

According to a preferred embodiment of the present disclosure, upon comparing the determined face postures, and judging whether the user is a living body according to a comparison result, the judging unit specifically performs: judge whether the determined face postures are consistent, and determine that the user is a living body if the determined face postures are consistent.

As can be seen from the above technical solutions, in the present disclosure, the face postures determined by the humidity sensor array and the face postures determined by the camera are compared to implement living body detection for the user.

DETAILED DESCRIPTION OF PREFERRED EMBODIMENTS

The present disclosure will be described in detail in conjunction with figures and specific embodiments to make objectives, technical solutions and advantages of the present disclosure more apparent.

Terms used in embodiments of the present disclosure are only intended to describe specific embodiments, not to limit the present disclosure. Singular forms "a", "said" and "the" used in embodiments and claims of the present disclosure are also intended to include plural forms, unless other senses are clearly defined in the context.

It should be appreciated that the term "and/or" used in the text is only an association relationship depicting associated objects and represents that three relations might exist, for example, A and/or B may represents three cases, namely, A exists individually, both A and B coexist, and B exists individually. In addition, the symbol "/" in the text generally indicates associated objects before and after the symbol are in an "or" relationship.

Depending on the context, the word "if" as used herein may be construed as "at the time when . . . " or "when . . . " or "responsive to determining" or "responsive to detecting". Similarly, depending on the context, phrases "if . . . is determined" or "if . . . (stated condition or event) is detected" may be construed as "when . . . is determined" or "responsive to determining" or "when . . . (stated condition or event) is detected" or "responsive to detecting (stated condition or event)".

Figure 1:
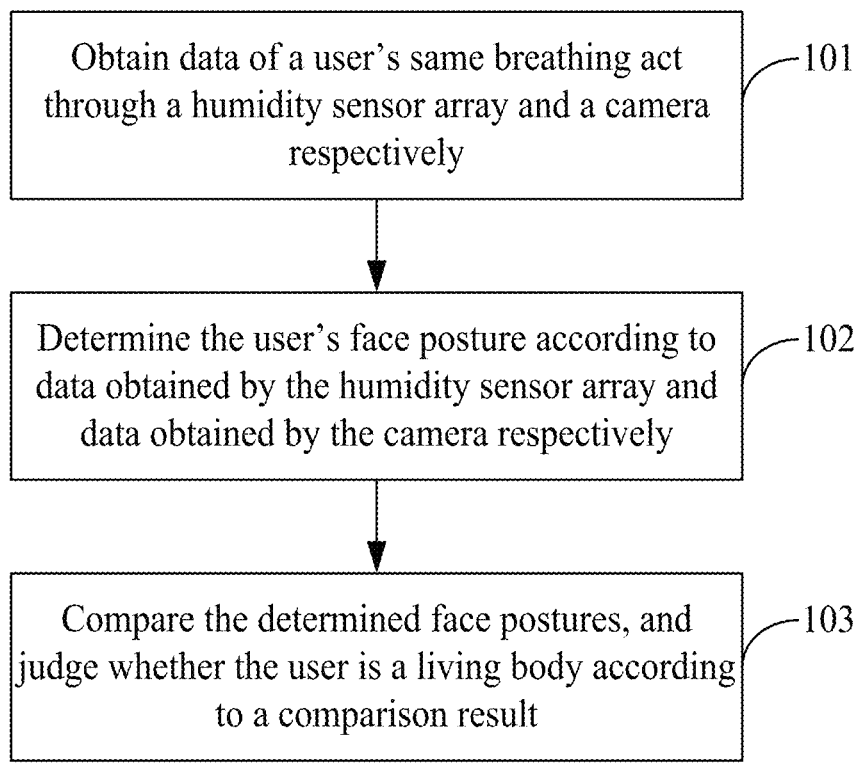
FIG. 1 is a flow chart of a living body detecting method according to an embodiment of the present disclosure.

FIG. 1 is a flow chart of a living body detecting method according to an embodiment of the present disclosure. As shown in FIG. 1, the method comprises:

At 101, obtain data of a user's same breathing act through a humidity sensor array and a camera respectively.

In this step, data of the user's breathing act is obtained through the humidity sensor array and the camera respectively.

Figure 2:
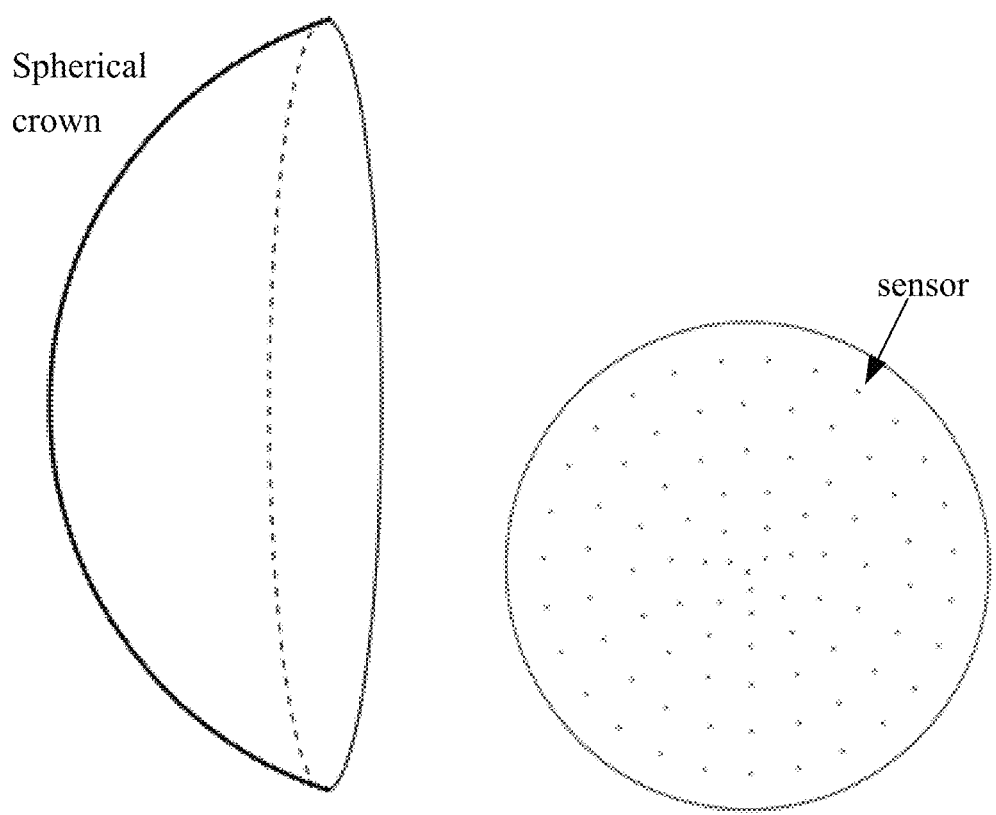
FIG. 2 is a schematic diagram of a humidity sensor array according to an embodiment of the present disclosure.

Specifically, the humidity sensor array may be comprised of a preset number of humidity sensors which are arranged in a specific shape, for example, humidity sensors evenly arranged on a spherical crown in a concentric circle form, as shown in FIG. 2. A left view in FIG. 2 is a schematic diagram of a shape of the spherical crown where the humidity sensor array lies, and a right view shows humidity sensors arranged in the crown, namely, the humidity sensor array as can be seen from the left view as seen from right. It can be seen from FIG. 2 that a preset number of humidity sensors are arranged on the spherical crown on the spherical crown in a concentric circle form (the crown is a portion of curved surface of a sphere), and the humidity sensors can sense changes of humidity in air so that the humidity sensor array obtains the data of the user's breathing act. It may be appreciated that in addition to even arrangement along the spherical crown in the concentric circle form, arrangement in a specific shape may employ even arrangement manners on a curved surface or plane in other shapes, for example, an even arrangement manner on a plane or an even arrangement manner on a curved surface in other shapes. In addition, the larger the number of humidity sensors in the humidity sensor array is, the more accurately the humidity sensors can obtain the data of the user's breathing act. Hence, the present disclosure does not limit the number of the humidity sensors.

Therefore, in this step, the data of the user's breathing act obtained by the humidity sensor array is: humidity change distribution data of the humidity sensor array caused by the user's breathing act at a specific location. That is, after the user makes a breathing act at a specific location, he cause surrounding air humidity to change, and the humidity sensors in the humidity sensor array can obtain humidity change distribution data according to the sensed humidity changes. The data of the user's breathing act obtained by the camera is one frame or several frames of image data obtained by shooting when the user makes the breathing act and including the user's face.

In this step, data obtained by the humidity sensor array and the camera is data of the user's same breathing act. It is possible that within a preset time period after the start of the detection, the data obtained by the humidity sensor array and the camera serves as data of the user's same breathing act. It is also possible that while the humidity sensors sense humidity changes, the camera shoots, and the data obtained by the humidity sensor array and the camera are regarded as data of the user's same breathing act.

The specific location is determined according to the arrangement manner of the humidity sensor array. When the humidity sensors are arranged evenly along the spherical crown in a concentric circle form, the specific location is a location nearby a spherical center of the spherical crown. For example, it is possible to set indication information or an indication device at the location nearby the spherical center, so that the user makes a breathing act according to the indication information or according to constraint of the indication device. Since the spherical crown is a portion of curved surface of the sphere, the spherical center of the spherical crown may be determined in a geometric manner. For example, it is possible to determine a whole sphere corresponding to the spherical crown according to the spherical crown, and thereby regard the spherical center of the determined sphere as the spherical center of the spherical crown. If the humidity sensors are evenly arranged on the plane, the specific location may be a location at a preset linear distance away from a center of the plane.

In 102, the user's face posture is determined according to the data obtained by the humidity sensor array and the data obtained by the camera respectively.

In this step, it is possible to determine the user's face posture, namely, face orientation when the user makes the breathing act, according to the data of the user's breathing act obtained by the humidity sensor array and data of the user's breathing act obtained by the camera respectively.

Optionally, when the user's face posture is determined according to data obtained by the humidity sensor array, the face orientation information is determined mainly according to the humidity change distribution data collected by the humidity sensor array. For example, it is feasible to employ the following manner: determine location information of the humidity sensors in the humidity sensor array that the humidity change value exceeds a preset threshold, namely, choose humidity sensors meeting a preset change requirement and then determine the location information of the selected humidity sensors, namely, the locations of the humidity sensors in the humidity sensor array; according to the specific location and the determined humidity sensor locations, determine space vectors pointing from the specific location to locations of the determined humidity sensors. Since the user's breathing act is made at the specific location, the space vectors determined between the specific location and the humidity sensor locations are used to represent the direction of the breathing act made by the user; the user's face posture is determined according to the space vectors: an angle between the space vectors and a preset reference surface is calculated, and the angle obtained from the calculation is determined as the user's face posture.

Figure 3:
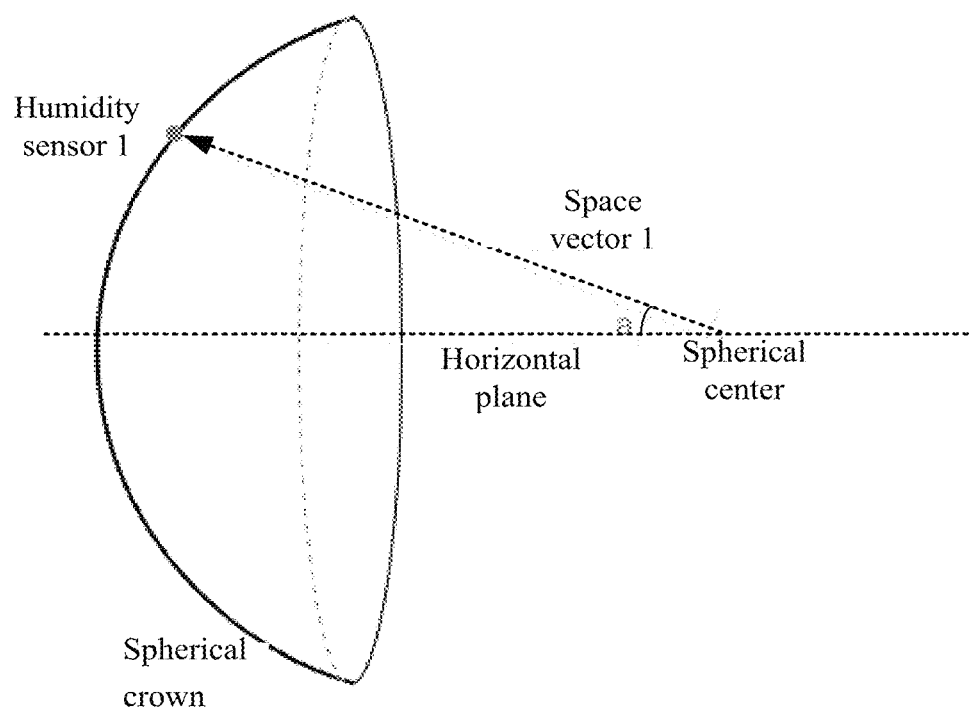
FIG. 3 and FIG. 4 each are a schematic diagram of determining a face posture according to a space vector according to an embodiment of the present disclosure.
Figure 4:
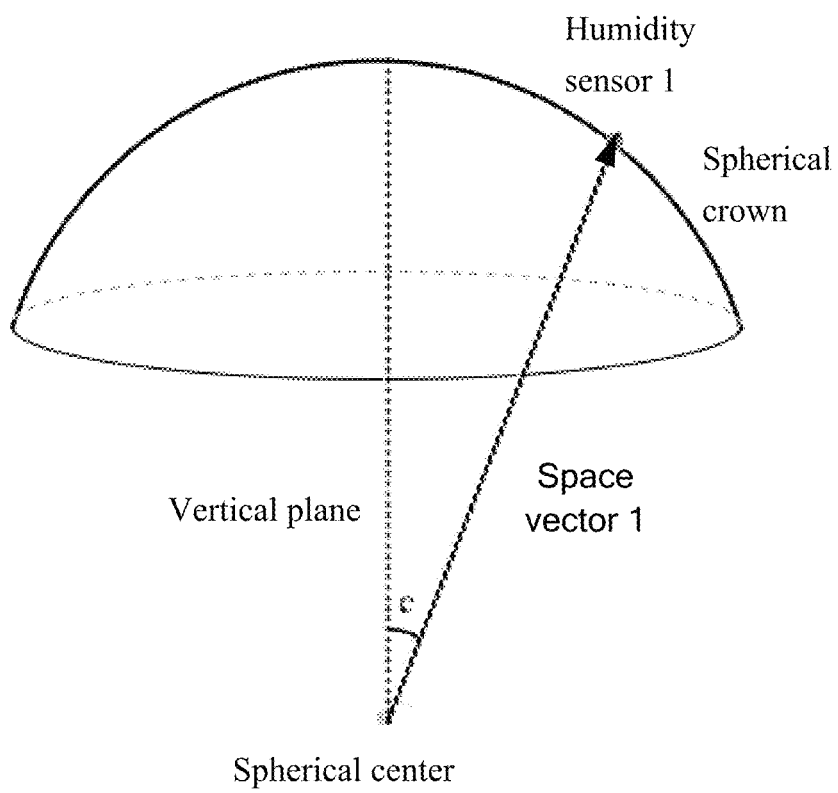

For example, as shown in FIG. 3, FIG. 3 is a front view of the spherical crown where the humidity sensor array lies. The humidity sensor array in FIG. 3 is arranged evenly along the spherical crown in a concentric circle form, and the specific location is a location nearby the spherical center of the spherical crown. Assuming that the humidity change value of the humidity sensor 1 exceeds a preset threshold, a horizontal plane passing through the spherical center serves as a first reference surface, and a space vector pointing from the spherical center to the humidity sensor 1 is represented by a space vector 1, an angle a between the space vector 1 and the first reference surface is obtained according to a space vector calculation formula. FIG. 4 is a top view of the spherical crown where the humidity sensor array lies. As shown in FIG. 4, assuming that a vertical surface passing through the spherical center is regarded as a second reference surface and the space vector pointing from the spherical center to the humidity sensor 1 is represented by the space vector 1, an angle c between the space vector 1 and the second reference surface is obtained according to a space vector calculation formula.

Optionally, when the user's face posture is determined according to the data obtained by the humidity sensor array, the following manner may be employed: determine identification information of humidity sensors in the humidity sensor array that the humidity change value exceeds a preset threshold, the identification information employing information such as serial number; determine the user's face posture according to a correspondence relationship between pre-configured identification information and the face posture.

The correspondence relationship between the identification information and the face posture may be preset in the following manner: pre-number respective humidity sensors in the humidity sensor array to obtain identification information of respective humidity sensors, then determine space vectors pointing from the specific location to respective humidity sensors, and calculate angles between respective space vectors and a preset reference surface. The calculation process is as stated above, and not detailed any more here. The angle may be regarded as the face posture information when the user breathes towards the direction of the humidity sensor; the correspondence relationship between the identification information and face posture is stored with respect to respective humidity sensors.

In this step, if in the humidity sensor array does not have humidity sensors that the humidity change value exceeds the preset threshold, i.e., if the user's breathing act might be too small to be sensed by the humidity sensor, or the user does not make the breathing act at the designated location, or the user does not breathe towards the humidity sensor array, the user is prompted to perform detection again.

In this step, if it is determined that there are a plurality of humidity sensors that the humidity change values exceed the preset threshold in the humidity sensor array, it is feasible to, according to a preset rule, select one humidity sensor from the plurality of humidity sensors, e.g., select a humidity sensor with a maximum humidity change value to determine the user's face posture. It is further possible to use the plurality of humidity sensors simultaneously to determine the user's face posture range, i.e., if there are a plurality of humidity sensors, since each humidity sensor corresponds to a different face posture, what is obtained through the plurality of humidity sensors is the face posture range. For example, if humidity change values of humidity sensors A, B and C exceed the preset threshold, it is feasible to obtain a face posture range from the face posture information determined according to humidity sensors A, B and C, and use the face posture range for subsequent comparison.

In this step, the camera may obtain the face posture in the following manner: according to an image captured when the user makes the breathing act, determine the user's face area in the image, for example, it is possible to detect the face in the image based on Haar-like feature or by using AdaBoost algorithm, to determine the face area; perform face posture detection for the face in the face area, for example, obtain the user's face posture in the face area by using a face alignment algorithm or by a method of matching based on feature points. Since the camera's collecting location and direction are fixed, the user's face posture in the space may be obtained based on the face posture from the image. This portion of content may be implemented by using already-existing technologies and not detailed any more here.

At the same time, when the face posture is obtained according to the camera-obtained data of the breathing act, it is further possible to use the face recognition algorithm to recognize the user's face to determine the user's identity, thereby achieving detection of whether the user is a living body while verifying the user's identity.

103 relates to comparing the determined face postures, and judging whether the user is a living body according to a comparison result.

In this step, it is feasible to compare face postures determined by the humidity sensor array and the camera, judge whether the face postures obtained by the humidity sensor array are consistent with the face postures obtained by the camera, and then determine whether the user is a living body according to a judgment result.

Since the face postures obtained by the humidity sensor array and the camera all are represented by using an angle, it is possible to judge whether the face postures obtained by the humidity sensor array are consistent with the face postures obtained by the camera in the following manner: when there is only one determined humidity sensor, compare whether a difference between a face posture angle obtained by the humidity sensor and a face posture angle obtained by the camera is within a preset range, and judge that the face postures are consistent if the difference is within the preset range; when there are a plurality of determined humidity sensors, judge whether the face posture angle determined by the camera is within a face posture range determined by the humidity sensors, and if yes, judge that the face postures are consistent.

Upon living body detection, the detection might fail due to shooting problems or the user's own reasons. Therefore, after this step, the method further comprises: prompting the user to perform detection again if the detection result is that the user is not the living body; if after preset times of detection, the obtained detection result is still that the user is not the living body, the user's detection result is that the user is not the living body. This manner can further improve the precision in detecting whether the user is the living body.

Figure 5:
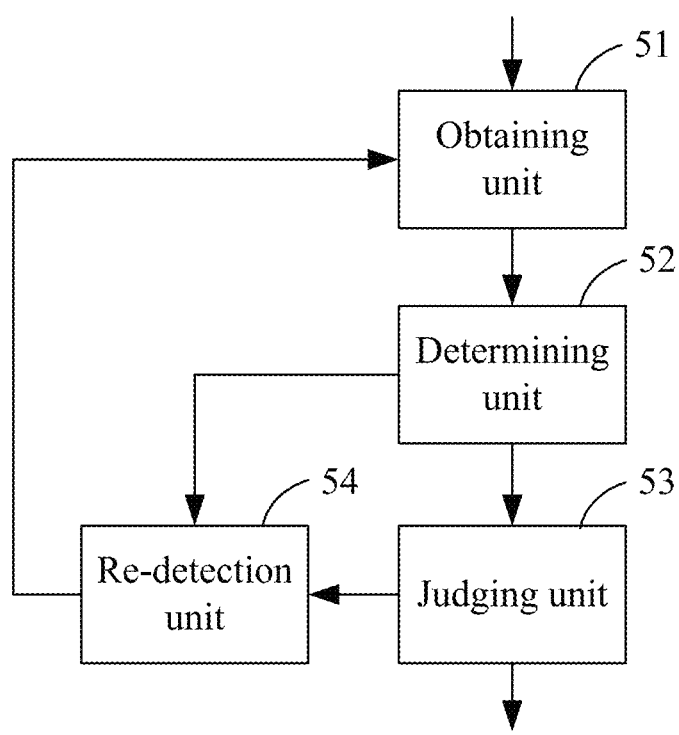
FIG. 5 is a structural schematic diagram of a living body detecting apparatus according to an embodiment of the present disclosure.

FIG. 5 is a structural schematic diagram of a living body detecting apparatus according to an embodiment of the present disclosure. As shown in FIG. 5, the apparatus comprises: an obtaining unit 51, a determining unit 52, a judging unit 53 and a re-detection unit 54.

The obtaining unit 51 is configured to obtain data of a user's same breathing act through a humidity sensor array and a camera respectively.

The obtaining unit 51 is configured to respectively obtain data of the user's breathing act through the humidity sensor array and the camera.

Specifically, the humidity sensor array in the obtaining unit 51 may be comprised of a preset number of humidity sensors which are arranged in a specific shape, for example, humidity sensors evenly arranged on a spherical crown in a concentric circle form. It may be appreciated that in addition to even arrangement along the spherical crown in the concentric circle form, arrangement in the specific shape may employ even arrangement manners on a curved surface or plane in other shapes, for example, an even arrangement manner on a plane or an even arrangement manner on a curved surface in other shapes. In addition, the larger the number of humidity sensors in the humidity sensor array is, the more accurately the humidity sensors can obtain the data of the user's breathing act. Hence, the present disclosure does not limit the number of the humidity sensors.

Therefore, the data of the user's breathing act obtained by the humidity sensor array in the obtaining unit 51 is: humidity change distribution data of the humidity sensor array caused by the user's breathing act at the specific location. That is, after the user makes a breathing act at a specific location, he cause surrounding air humidity to change, and the humidity sensors in the humidity sensor array in the obtaining unit 51 can obtain humidity change distribution data according to the sensed humidity changes. The data of the user's breathing act obtained by the camera in the obtaining unit 51 is one frame or several frames of image data obtained by shooting when the user makes the breathing act and including the user's face.

Data obtained by the humidity sensor array in the obtaining unit 51 and the camera is data of the user's same breathing act. The obtaining unit 51 may, within a preset time period after the start of the detection, regard the data obtained by the humidity sensor array and the camera as data of the user's same breathing act. The obtaining unit 51 may further regard the data obtained by the humidity sensor array and the camera as data of the user's same breathing act, when the camera shoots while the humidity sensors sense humidity changes.

The specific location is determined according to the arrangement manner of the humidity sensor array. When the humidity sensors in the obtaining unit 51 are arranged evenly along the spherical crown in a concentric circle form, the specific location is a location nearby a spherical center of the spherical crown. For example, it is possible to set indication information or an indication device at the location nearby the spherical center, so that the user makes a breathing act according to the indication information or according to constraint of the indication device. Since the spherical crown is a portion of curved surface of the sphere, the spherical center of the spherical crown may be determined in a geometric manner. For example, it is possible to determine a whole sphere corresponding to the spherical crown according to the spherical crown, and thereby regard the spherical center of the determined sphere as the spherical center of the spherical crown. If the humidity sensors in the obtaining unit 51 are evenly arranged on the plane, the specific location may be a location at a preset linear distance away from a center of the plane.

The determining unit 52 is configured to determine the user's face posture according to the data obtained by the humidity sensor array and the data obtained by the camera respectively.

The determining unit 52 determines the user's face posture, namely, face orientation when the user makes the breathing act, according to the data of the user's breathing act obtained by the humidity sensor array and data of the user's breathing act obtained by the camera respectively.

Optionally, when the determining unit 52 determines the user's face posture according to data obtained by the humidity sensor array, the face orientation information is determined mainly according to the humidity change distribution data collected by the humidity sensor array. For example, it is feasible to employ the following manner: determine location information of the humidity sensors in the humidity sensor array that the humidity change value exceeds a preset threshold, namely, choose humidity sensors meeting a preset change requirement and then determine the location information of the selected humidity sensors, namely, the locations of the humidity sensors in the humidity sensor array; according to the specific location and the determined humidity sensor locations, determine space vectors pointing from the specific location to locations of the determined humidity sensors. Since the user's breathing act is made at the specific location, the space vectors determined between the specific location and the humidity sensor locations are used to represent the direction of the breathing act made by the user; the user's face posture is determined according to the space vectors: an angle between the space vectors and a preset reference surface is calculated, and the angle obtained from the calculation is determined as the user's face posture.

Optionally, when the determining unit 52 determines the user's face posture according to the data obtained by the humidity sensor array, the following manner may be employed: determine identification information of humidity sensors in the humidity sensor array that the humidity change value exceeds a preset threshold, the identification information employing information such as serial number; determine the user's face posture according to a correspondence relationship between pre-configured identification information and the face posture.

The correspondence relationship between the identification information and the face posture may be preset in the following manner: pre-number respective humidity sensors in the humidity sensor array to obtain identification information of respective humidity sensors, then determine space vectors pointing from the specific location to respective humidity sensors, and calculate angles between respective space vectors and a preset reference surface. The calculation process is as stated above, and not detailed any more here. The angle may be regarded as the face posture information when the user breathes towards the direction of the humidity sensor; the correspondence relationship between the identification information and face posture is stored with respect to respective humidity sensors.

If the determining unit 52 determines that there are a plurality of humidity sensors that the humidity change values exceed the preset threshold in the humidity sensor array, it is feasible to, according to a preset rule, select one humidity sensor from the plurality of humidity sensors, e.g., the determining unit 52 selects a humidity sensor with a maximum humidity change value to determine the user's face posture. It is further possible to use the plurality of humidity sensors simultaneously to determine the user's face posture range, i.e., if there are a plurality of humidity sensors, since each humidity sensor corresponds to a different face posture, what is obtained by the determining unit 52 through the plurality of humidity sensors is the face posture range. For example, if humidity change values of humidity sensors A, B and C exceed the preset threshold, it is feasible to obtain a face posture range from the face posture information determined according to humidity sensors A, B and C, and use the face posture range for subsequent comparison.

Upon obtaining the face posture according to the data of the breathing act obtained by the camera, the determining unit 52 may employ the following manner: according to an image captured by the camera when the user makes the breathing act, determine the user's face area in the image, for example, it is possible to detect the face in the image based on Haar-like feature or by using AdaBoost algorithm, to determine the face area; perform face posture detection for the face in the face area, for example, obtain the user's face posture in the face area by using a face alignment algorithm or by a method of matching based on feature points. Since the camera's collecting location and direction are fixed, the user's face posture in the space may be obtained based on the face posture from the image. This portion of content may be implemented by using already-existing technologies and not detailed any more here.

At the same time, when the determining unit 52 obtains the face posture according to the camera-obtained data of the breathing act, it is further possible to use the face recognition algorithm to recognize the user's face to determine the user's identity, thereby achieving detection of whether the user is a living body while verifying the user's identity.

The judging unit 53 is configured to compare the determined face postures, and judge whether the user is a living body according to a comparison result.

The judging unit 53 compares face postures determined by the humidity sensor array and the camera, judge whether the face postures obtained by the humidity sensor array are consistent with the face postures obtained by the camera, and then determine whether the user is a living body according to a judgment result.

Since the face postures obtained by the humidity sensor array and the camera all are represented by using an angle, the judging unit 53 may judge whether the face postures are consistent in the following manner: when there is only one determined humidity sensor, the judging unit 53 compares whether a difference between a face posture angle obtained by the humidity sensor and a face posture angle obtained by the camera is within a preset range, and judge that the face postures are consistent if the difference is within the preset range; when there are a plurality of determined humidity sensors, the judging unit 53 judges whether the face posture angle determined by the camera is within a face posture range determined by the humidity sensors, and if yes, judge that the face postures are consistent.

The re-detection unit 54 is configured to prompt the user to perform detection again if the detection result is that the user is not the living body.

If the determining unit 52 fails to select, from the humidity sensor array, humidity sensors that the humidity change value exceeds the preset threshold, i.e., if the user's breathing act might be too small to be sensed by the humidity sensor, or the user does not make the breathing act at the designated location, or the user does not breathe towards the humidity sensor array, the re-detection unit 54 prompts the user to perform detection again; meanwhile, when the judging unit 53 judges that the user is not a living body, the re-detection unit 54 prompts the user to perform detection again. If after preset times of detection, the obtained detection result is still that the user is not the living body, the user's detection result is that the user is not the living body. This manner can further improve the precision in detecting whether the user is the living body.

An application scenario is listed here:

Currently, the user's identity is manually verified at the security check site of the airport, to prove that the user is the user himself. When the manner provided by the embodiments of the present disclosure is employed, it is possible to dispose the humidity sensor array and the camera at the security check site, implement detection of whether the user is a living body according to the face postures determined by the humidity sensor array and the camera, and implement recognition of the user's identity through the user's images shot by the camera. Only when user identity recognition and living body detection both pass can the security check door be opened, and can the user get in.

Figure 6:
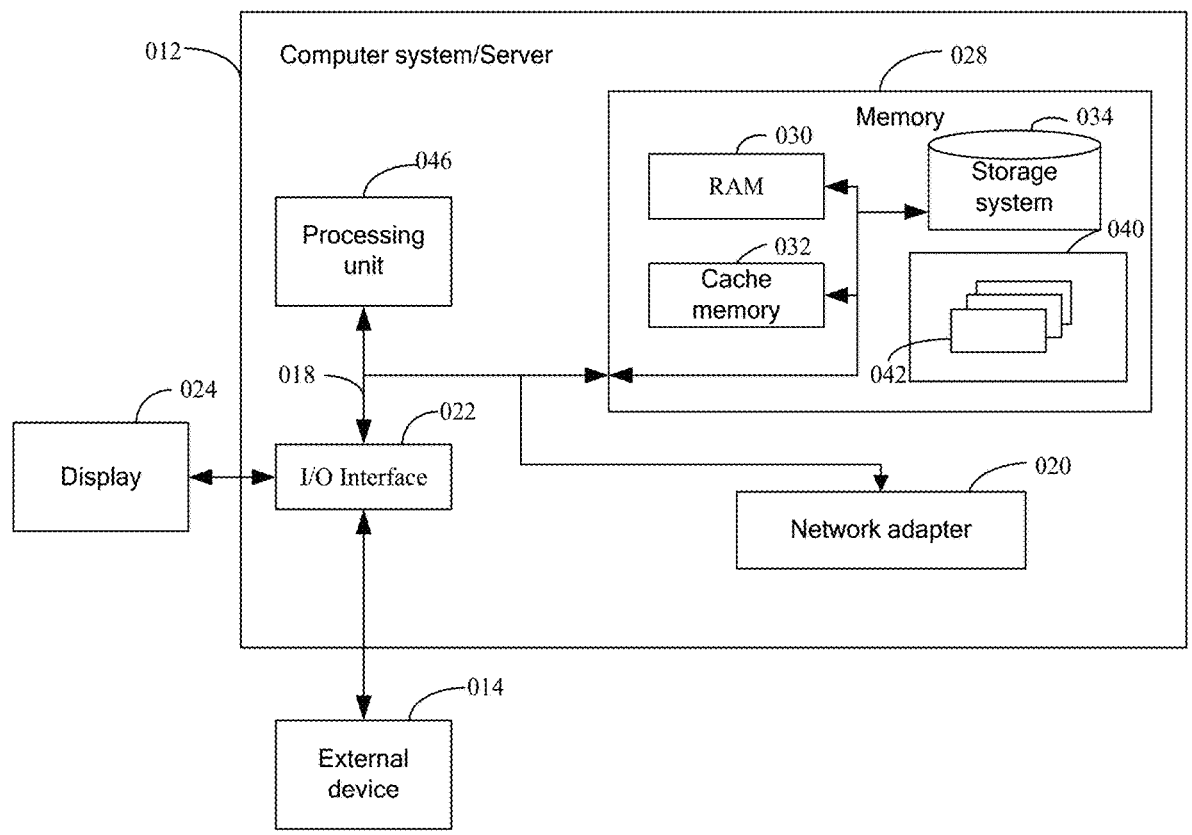
FIG. 6 is a block diagram of a computer system/server according to an embodiment of the present disclosure.

FIG. 6 illustrates a block diagram of an example computer system/server 012 adapted to implement an implementation mode of the present disclosure. The computer system/server 012 shown in FIG. 6 is only an example and should not bring about any limitation to the function and scope of use of the embodiments of the present disclosure.

As shown in FIG. 6, the computer system/server 012 is shown in the form of a general-purpose computing device. The components of computer system/server 012 may include, but are not limited to, one or more processors (processing units) 016, a system memory 028, and a bus 018 that couples various system components including system memory 028 and the processor 016.

Bus 018 represents one or more of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 012 typically includes a variety of computer system readable media. Such media may be any available media that is accessible by computer system/server 012, and it includes both volatile and non-volatile media, removable and non-removable media.

The system memory 028 can include computer system readable media in the form of volatile memory, such as random access memory (RAM) 030 and/or cache memory 032. Computer system/server 012 may further include other removable/non-removable, volatile/non-volatile computer system storage media. By way of example only, storage system 034 can be provided for reading from and writing to a non-removable, non-volatile magnetic media (not shown in FIG. 6 and typically called a "hard drive"). Although not shown in FIG. 6, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each drive can be connected to bus 018 by one or more data media interfaces. The memory 028 may include at least one program product having a set (e.g., at least one) of program modules that are configured to carry out the functions of embodiments of the present disclosure.

Program/utility 040, having a set (at least one) of program modules 042, may be stored in the system memory 028 by way of example, and not limitation, as well as an operating system, one or more disclosure programs, other program modules, and program data. Each of these examples or a certain combination thereof might include an implementation of a networking environment. Program modules 042 generally carry out the functions and/or methodologies of embodiments of the present disclosure.

Computer system/server 012 may also communicate with one or more external devices 014 such as a keyboard, a pointing device, a display 024, etc. In the present disclosure, the computer system/server 012 communicates with an external radar device, or with one or more devices that enable a user to interact with computer system/server 012; and/or with any devices (e.g., network card, modem, etc.) that enable computer system/server 012 to communicate with one or more other computing devices. Such communication can occur via Input/Output (I/O) interfaces 022. Still yet, computer system/server 012 can communicate with one or more networks such as a local area network (LAN), a general wide area network (WAN), and/or a public network (e.g., the Internet) via a network adapter 020. As depicted in the figure, network adapter 020 communicates with the other communication modules of computer system/server 012 via the bus 018. It should be understood that although not shown, other hardware and/or software modules could be used in conjunction with computer system/server 012. Examples, include, but are not limited to: microcode, device drivers, redundant processing units, external disk drive arrays, RAID systems, tape drives, and data archival storage systems, etc.

The processing unit 016 executes various function applications and data processing by running programs stored in the system memory 028, for example, implements the living body detecting method, which may comprise:

obtaining data of a user's same breathing act through a humidity sensor array and a camera respectively;

determining the user's face posture according to data obtained by the humidity sensor array and data obtained by the camera respectively;

comparing the determined face postures, and judging whether the user is a living body according to a comparison result.

The above-mentioned computer program may be disposed in a computer storage medium, i.e., the computer storage medium is encoded with a computer program. When the program, executed by one or more computers, enables said one or more computers to execute steps of methods and/or operations of apparatuses as shown in the above embodiments of the present disclosure. For example, steps of the method executed by said one or more processors may include:

obtaining data of a user's same breathing act through a humidity sensor array and a camera respectively;

determining the user's face posture according to data obtained by the humidity sensor array and data obtained by the camera respectively;

comparing the determined face postures, and judging whether the user is a living body according to a comparison result.

As time goes by and technologies develop, the meaning of medium is increasingly broad. A propagation channel of the computer program is no longer limited to tangible medium, and it may also be directly downloaded from the network. The computer-readable medium of the present embodiment may employ any combinations of one or more computer-readable media. The machine readable medium may be a computer readable signal medium or a computer readable storage medium. A computer readable medium for example may include, but not limited to, an electronic, magnetic, optical, electromagnetic, infrared, or semiconductor system, apparatus, or device, or any suitable combination of the foregoing. More specific examples (non-exhaustive listing) of the computer readable storage medium would include an electrical connection having one or more conductor wires, a portable computer magnetic disk, a hard disk, a random access memory (RAM), a read-only memory (ROM), an erasable programmable read-only memory (EPROM or Flash memory), optical fiber, a portable compact disc read-only memory (CD-ROM), an optical storage device, a magnetic storage device, or any suitable combination of the foregoing. In the text herein, the computer readable storage medium can be any tangible medium that includes or stores a program. The program may be used by an instruction execution system, apparatus or device or used in conjunction therewith.

The computer-readable signal medium may be included in a baseband or serve as a data signal propagated by part of a carrier, and it carries a computer-readable program code therein. Such propagated data signal may take many forms, including, but not limited to, electromagnetic signal, optical signal or any suitable combinations thereof. The computer-readable signal medium may further be any computer-readable medium besides the computer-readable storage medium, and the computer-readable medium may send, propagate or transmit a program for use by an instruction execution system, apparatus or device or a combination thereof.

The program codes included by the computer-readable medium may be transmitted with any suitable medium, including, but not limited to, radio, electric wire, optical cable, RF or the like, or any suitable combination thereof. Computer program code for carrying out operations disclosed herein may be written in one or more programming languages or any combination thereof. These programming languages include an object oriented programming language such as Java, Smalltalk, C++ or the like, and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The technical solutions according to the present disclosure may be employed to perform living body detection for the user by comparing the face postures determined by the humidity sensor array and the camera while performing identity recognition for the user.

In the embodiments provided by the present disclosure, it should be understood that the revealed system, apparatus and method can be implemented in other ways. For example, the above-described embodiments for the apparatus are only exemplary, e.g., the division of the units is merely logical one, and, in reality, they can be divided in other ways upon implementation.

The units described as separate parts may be or may not be physically separated, the parts shown as units may be or may not be physical units, i.e., they can be located in one place, or distributed in a plurality of network units. One can select some or all the units to achieve the purpose of the embodiment according to the actual needs.

Further, in the embodiments of the present disclosure, functional units can be integrated in one processing unit, or they can be separate physical presences; or two or more units can be integrated in one unit. The integrated unit described above can be implemented in the form of hardware, or they can be implemented with hardware plus software functional units.

The aforementioned integrated unit in the form of software function units may be stored in a computer readable storage medium. The aforementioned software function units are stored in a storage medium, including several instructions to instruct a computer device (a personal computer, server, or network equipment, etc.) or processor to perform some steps of the method described in the various embodiments of the present disclosure. The aforementioned storage medium includes various media that may store program codes, such as U disk, removable hard disk, Read-Only Memory (ROM), a Random Access Memory (RAM), magnetic disk, or an optical disk.

What are stated above are only preferred embodiments of the present disclosure and not intended to limit the present disclosure. Any modifications, equivalent substitutions and improvements made within the spirit and principle of the present disclosure all should be included in the extent of protection of the present disclosure.

What is claimed is:

1. A living body detecting method, wherein the method comprises:
   obtaining data of a user's same breathing act through a humidity sensor array and a camera respectively;
   determining the user's face posture according to data obtained by the humidity sensor array and data obtained by the camera respectively;
   comparing the determined face postures, and judging whether the user is a living body according to a comparison result.

2. The method according to claim 1, wherein the humidity sensor array comprises a preset number of humidity sensors which are arranged in a specific shape.

3. The method according to claim 2, wherein the arrangement in a specific shape comprises: even arrangement along a spherical crown in a concentric circle form.

4. The method according to claim 1, wherein the obtaining data of the user's breathing act through the humidity sensor array comprises:
   obtaining humidity change distribution data of the humidity sensor array caused by the user's breathing act at a specific location.

5. The method according to claim 4, wherein the humidity sensor array comprises a preset number of humidity sensors which are arranged evenly along a spherical crown in a concentric circle form;
   the specific location is a location nearby a spherical center of the spherical crown.

6. The method according to claim 5, wherein the determining the user's face posture according to data obtained by the humidity sensor array comprises:
   determining location information of the humidity sensors in the humidity sensor array that humidity change values exceed a preset threshold;
   according to the specific location and locations of the determined humidity sensors, determining space vectors pointing from the specific location to the locations of the determined humidity sensors;
   determining the user's face posture according to the space vectors.

7. The method according to claim 5, wherein the determining the user's face posture according to data obtained by the humidity sensor array comprises:
   determining identification information of humidity sensors in the humidity sensor array that humidity change values exceed a preset threshold;

determining the user's face posture according to a correspondence relationship between pre-configured identification information and the face posture.

8. The method according to claim 6, wherein the method further comprises:
prompting the user to perform detection again if the humidity sensor array does not include humidity sensors that humidity change values exceed the present threshold.

9. The method according to claim 6, wherein if it is determined that there are a plurality of humidity sensors that the humidity change values exceed the preset threshold in the humidity sensor array, the method comprises:
according to a preset rule, selecting one humidity sensor from the plurality of humidity sensors to determine the user's face posture; or
using the plurality of humidity sensors to determine the user's face posture range.

10. The method according to claim 1, wherein the method further comprises:
using the data obtained by the camera to perform face recognition to determine the user's identity.

11. The method according to claim 1, wherein the comparing the determined face postures and judging whether the user is a living body according to a comparison result comprises:
judging whether the determined face postures are consistent, and determining that the user is a living body if the determined face postures are consistent.

12. A computer device, comprising a memory, a processor and a computer program which is stored on the memory and runnable on the processor, wherein the processor, upon executing the program, implements a living body detecting method, wherein the method comprises:
obtaining data of a user's same breathing act through a humidity sensor array and a camera respectively;
determining the user's face posture according to data obtained by the humidity sensor array and data obtained by the camera respectively;
comparing the determined face postures, and judging whether the user is a living body according to a comparison result.

13. The computer device according to claim 12, wherein the humidity sensor array comprises a preset number of humidity sensors which are arranged in a specific shape.

14. The method according to claim 13, wherein the arrangement in a specific shape comprises: even arrangement along a spherical crown in a concentric circle form.

15. The computer device according to claim 12, wherein the obtaining data of the user's breathing act through the humidity sensor array comprises:
obtaining humidity change distribution data of the humidity sensor array caused by the user's breathing act at a specific location.

16. The computer device according to claim 15, wherein the humidity sensor array comprises a preset number of humidity sensors which are arranged evenly along a spherical crown in a concentric circle form;
the specific location is a location nearby a spherical center of the spherical crown.

17. The computer device according to claim 16, wherein the determining the user's face posture according to data obtained by the humidity sensor array comprises:

determining location information of the humidity sensors in the humidity sensor array that humidity change values exceed a preset threshold;
according to the specific location and locations of the determined humidity sensors, determining space vectors pointing from the specific location to the locations of the determined humidity sensors;
determining the user's face posture according to the space vectors.

18. The computer device according to claim 16, wherein the determining the user's face posture according to data obtained by the humidity sensor array comprises:
determining identification information of humidity sensors in the humidity sensor array that humidity change values exceed a preset threshold;
determining the user's face posture according to a correspondence relationship between pre-configured identification information and the face posture.

19. The computer device according to claim 17, wherein the method further comprises:
prompting the user to perform detection again if the humidity sensor array does not include humidity sensors that humidity change values exceed the present threshold.

20. The computer device according to claim 7, wherein if it is determined that there are a plurality of humidity sensors that the humidity change values exceed the preset threshold in the humidity sensor array, the method comprises:
according to a preset rule, selecting one humidity sensor from the plurality of humidity sensors to determine the user's face posture; or
using the plurality of humidity sensors to determine the user's face posture range.

21. The computer device according to claim 12, wherein the method further comprises:
using the data obtained by the camera to perform face recognition to determine the user's identity.

22. The computer device according to claim 12, wherein the comparing the determined face postures and judging whether the user is a living body according to a comparison result comprises:
judging whether the determined face postures are consistent, and determining that the user is a living body if the determined face postures are consistent.

23. The computer device according to claim 12, wherein the computer device further comprises:
a camera for collecting images;
a humidity sensor array for collecting humidity data.

24. A non-transitory computer readable storage medium containing computer-executable instructions, the computer-executable instructions, when executed by a computer processor, implementing a living body detecting method, wherein the method comprises:
obtaining data of a user's same breathing act through a humidity sensor array and a camera respectively;
determining the user's face posture according to data obtained by the humidity sensor array and data obtained by the camera respectively;
comparing the determined face postures, and judging whether the user is a living body according to a comparison result.

* * * * *